(12) United States Patent
Fujita et al.

(10) Patent No.: US 6,812,821 B2
(45) Date of Patent: Nov. 2, 2004

(54) HUMIDITY SENSOR

(75) Inventors: Hiroki Fujita, Komaki (JP); Tetsuo Yamada, Kasugai (JP); Satoshi Sugaya, Kounan (JP); Kenji Kato, Nagoya (JP); Noboru Ishida, Kagamigahara (JP); Takafumi Oshima, Nagoya (JP)

(73) Assignee: NGK Spark Plug Co., Ltd., Aichi (JP)

( * ) Notice: Subject to any disclaimer, the term of this patent is extended or adjusted under 35 U.S.C. 154(b) by 0 days.

(21) Appl. No.: 10/157,134

(22) Filed: May 30, 2002

(65) Prior Publication Data

US 2002/0190840 A1 Dec. 19, 2002

(30) Foreign Application Priority Data

May 31, 2001 (JP) ..................................... P. 2001-165318
May 31, 2001 (JP) ..................................... P.2001-165319

(51) Int. Cl.$^7$ ................................................. H01C 7/00
(52) U.S. Cl. ........................ 338/34; 73/335.05; 338/35
(58) Field of Search ...................... 73/335.05; 338/34, 338/35

(56) References Cited

U.S. PATENT DOCUMENTS

| | | | |
|---|---|---|---|
| 3,691,301 A | * 9/1972 | Fraioli | 379/114 |
| 3,864,659 A | * 2/1975 | Furuuchi et al. | 338/35 |
| 4,017,820 A | * 4/1977 | Ross | 338/35 |
| 4,277,742 A | * 7/1981 | Kovac et al. | 324/689 |
| 4,326,414 A | * 4/1982 | Terada et al. | 73/335.05 |
| 4,356,150 A | 10/1982 | Johnson et al. | |
| 4,481,813 A | 11/1984 | Tanei et al. | |
| 4,482,581 A | * 11/1984 | Lorin et al. | 427/79 |
| 4,528,543 A | * 7/1985 | Miyoshi et al. | 338/35 |
| 4,656,455 A | * 4/1987 | Tanino et al. | 338/35 |
| 4,666,628 A | * 5/1987 | Uchikawa | 252/500 |
| 4,723,439 A | * 2/1988 | Asakura et al. | 73/29.05 |
| 4,794,323 A | * 12/1988 | Zhou et al. | 324/71.5 |
| 5,001,453 A | * 3/1991 | Ikejiri et al. | 338/35 |
| 5,136,274 A | * 8/1992 | Shimomura et al. | 338/35 |
| 5,334,350 A | * 8/1994 | Friese et al. | 422/98 |
| 5,367,283 A | * 11/1994 | Lauf et al. | 338/34 |
| 5,607,564 A | * 3/1997 | Stormbom | 204/284 |
| 5,969,231 A | * 10/1999 | Qu et al. | 73/31.05 |
| 6,073,480 A | * 6/2000 | Gokhfeld | 73/29.02 |
| 6,120,891 A | * 9/2000 | Balkus, Jr. et al. | 428/336 |
| 6,229,318 B1 | * 5/2001 | Suda | 324/696 |
| 2002/0040598 A1 | * 4/2002 | Sugaya et al. | |

FOREIGN PATENT DOCUMENTS

| | | |
|---|---|---|
| EP | 0 875 752 A1 | 11/1998 |
| EP | 1197748 | * 4/2002 |
| JP | 02306151 | 12/1990 |

OTHER PUBLICATIONS

JP03054444 english abstract (Mar. 1991).*
European Search Report for EP 02 01 1947 dated Jun. 2, 2003.

* cited by examiner

*Primary Examiner*—Karl D. Easthom
(74) *Attorney, Agent, or Firm*—Sughrue Mion, PLLC

(57) ABSTRACT

A humidity sensor comprising an insulating substrate, a detection electrodes and a moisture-sensitive layer, wherein the moisture-sensitive layer is a porous layer and has a thickness not greater than 200 $\mu$m.

25 Claims, 8 Drawing Sheets

CROSS-SECTIONAL VIEW
TAKEN ALONG LINE A-A'

ELECTRICALLY INSULATING SUBSTRATE (Al₂O₃)

CROSS-SECTIONAL VIEW TAKEN ALONG LINE A-A'

CROSS-SECTIONAL VIEW
TAKEN ALONG LINE A-A'

HUMIDITY SENSOR

FIELD OF THE INVENTION

The present invention relates to a humidity sensor for measuring the moisture content of an atmosphere by means of change in an electrical resistance of a moisture-sensitive layer. The humidity sensor can be used, for example, for measuring the moisture content of air; the moisture content of exhaust gas in an exhaust pipe of an internal combustion engine of, for example, an automobile, ship, or airplane; or the moisture content of, for example, an atmosphere surrounding a fuel electrode or an air electrode or an atmosphere in a pipe of a fuel cell.

BACKGROUND OF THE INVENTION

Typically employed humidity sensors include resistance-variable-type humidity sensors utilizing adsorption and desorption of water molecules; and capacitance-variable-type humidity sensors utilizing change in capacitance. Such humidity sensors are formed from a moisture sensitive material such as $Al_2O_3$, $MgCr_2O_4$—$TiO_2$, $TiO_2$—$V_2O_5$, or $ZrCr_2O_4$—$LiZrVO_4$. Most of the humidity sensors measure a change in electric resistance.

Humidity sensors formed from such moisture sensitive ceramic materials are typically fabricated by a method described in, for example, Japanese Patent Publication (kokoku) No. 1989-22965. Specifically, a lower electrode is formed on an insulating substrate; a moisture-sensitive layer is formed through pelleting or a like process in such a manner as to overlie the lower electrode; and an upper electrode is formed on the upper surface of the moisture-sensitive layer. A humidity sensor whose detection electrodes each assume a comblike shape is also known.

SUMMARY OF THE INVENTION

Such conventional humidity sensors can be used in the ordinary atmosphere or the like without involvement of problems. However, the conventional humidity sensors involve problems, such as low-precision measurement and impaired response, in application to measurement in an atmosphere which exhibits significant temperature variation (e.g. −40 to 750° C.), very low oxygen concentration, and significant variations in, for example, gas flow velocity, gas flow rate, and gas pressure, as in an exhaust pipe of an automobile, or in application to measurement in an atmosphere which contains a considerable amount of reducing gas, such as an atmosphere surrounding a fuel electrode of a fuel cell. In application to measurement in such an atmosphere, a humidity sensor must exhibit excellent thermal shock resistance in addition to sufficiently good response. A conventional humidity sensor including a moisture-sensitive layer formed through pelleting or a common thick-film-type humidity sensor fails to detect accurately and at highly good response a change in electrical resistance of the moisture-sensitive layer which is induced by the moisture content of an atmosphere to be measured, and fails to exhibit sufficient strength in relation to thermal shock resistance, etc.

The present invention contemplates solving the aforementioned conventional problems. An object of the present invention is to provide a humidity sensor capable of exhibiting highly good response and excellent strength in relation to, for example, thermal shock resistance, and capable of maintaining stable moisture sensitivity over a long period of time, even in application to measurement in an atmosphere which exhibits significant temperature variation, very low oxygen concentration, and significant variations in, for example, gas flow velocity, gas flow rate, and gas pressure, as in an exhaust pipe of a vehicle.

When the moisture-sensitive layer of a humidity sensor assumes the form of a thin layer having a certain thickness, the humidity sensor can exhibit enhanced response, and thermal stress can be reduced. When the detection electrodes of the humidity sensor are formed of a porous material that is formed from a noble metal, such as Pt or Au which exhibits excellent heat resistance and corrosion resistance and has an average pore size greater than that of the moisture-sensitive layer, strong adhesion can be attained among an insulating substrate, the detection electrodes, and the moisture-sensitive layer while excellent response, for example, is maintained intact. Even in application to measurement in a specific atmosphere as in an exhaust pipe of a vehicle, such a humidity sensor can exhibit high accuracy, highly good response, and sufficient strength in relation to, for example, thermal shock resistance, and can maintain excellent humidity detection performance over a long period of time.

The present invention has been accomplished on the basis of this finding.

(1a) Schematic perspective view showing a humidity sensor having electrodes formed on the upper and lower surfaces of a moisture-sensitive layer. (1b) Cross-sectional view of the humidity sensor taken along line A-A' in FIG. 1a.

Figure 2A:
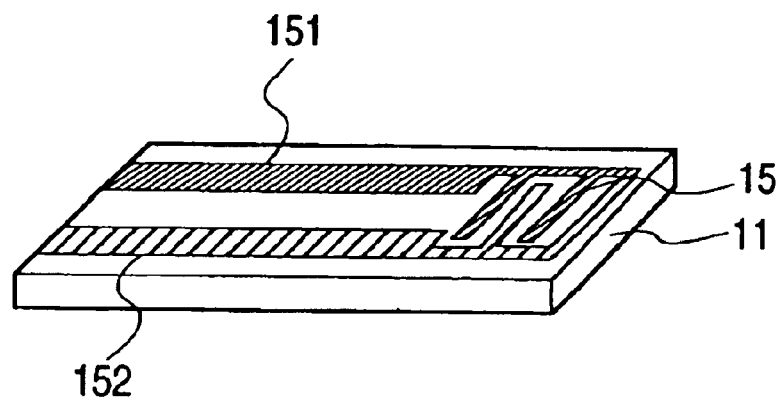
Figure 2B:
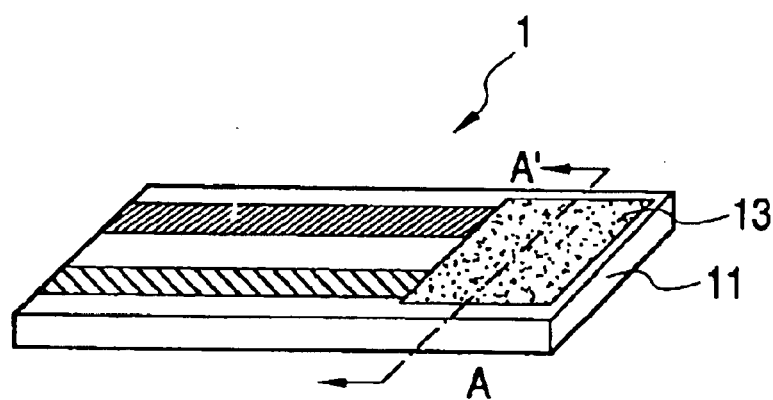
Figure 2C:
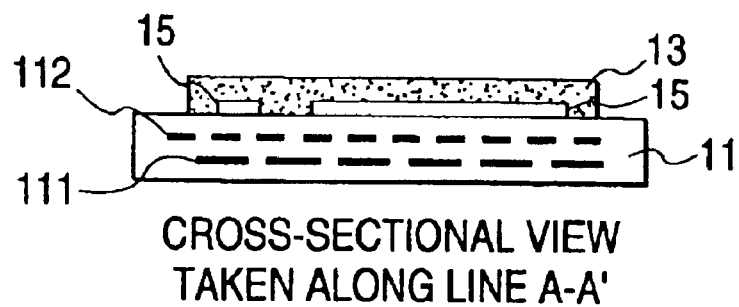

[FIGS. 2a, 2b and 2c]

(2a) Schematic perspective view showing comblike electrodes formed on an insulating substrate. (2b) Schematic perspective view showing a humidity sensor formed through additional formation of a moisture-sensitive layer on the product of FIG. 2a. (2c) Cross-sectional view of the humidity sensor taken along line A-A' in FIG. 2b.

[FIG. 3]

Graph showing comparison of change of sensor resistance with relative humidity between Example and Comparative Example.

[FIG. 4]

Graph showing comparison of response characteristic as represented by sensor output reduced to humidity between Examples and Comparative Example.

[FIG. 5]

Figure 4:
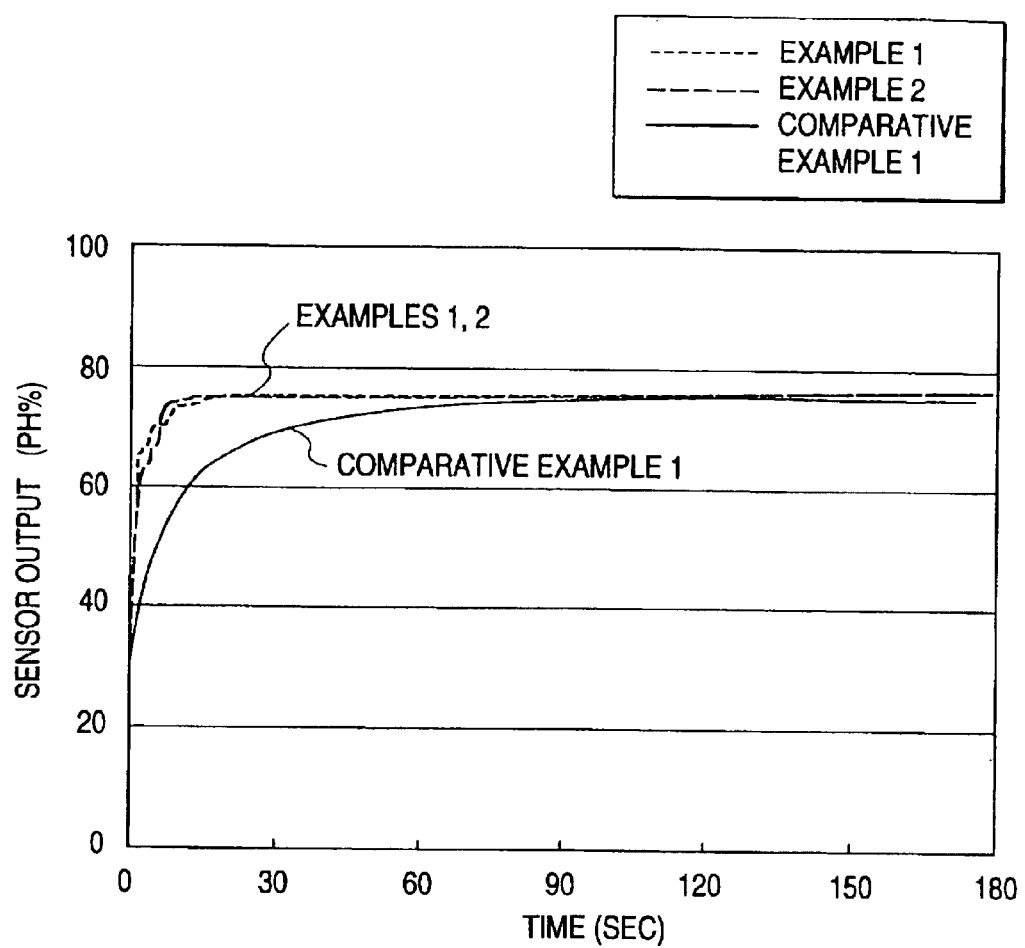

Enlarged graph showing a portion of the graph of FIG. 4 corresponding to a region of short response time.

[FIG. 6]

Graph showing interrelation between response characteristic as represented by sensor output reduced to humidity and the thickness of a moisture-sensitive layer.

[FIG. 7]

Schematic explanatory view showing diffusion of a gas to be measured within a moisture-sensitive layer.

[FIG. 8]

Schematic representation showing an apparatus for evaluating initial characteristics, etc. of a humidity sensor by means of a diffluence method.

Figure 9A:
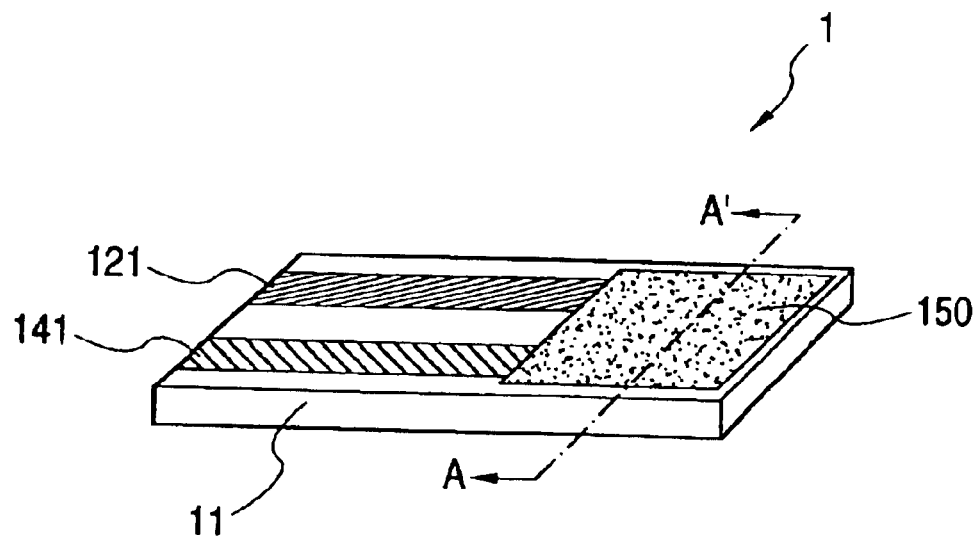
Figure 9B:
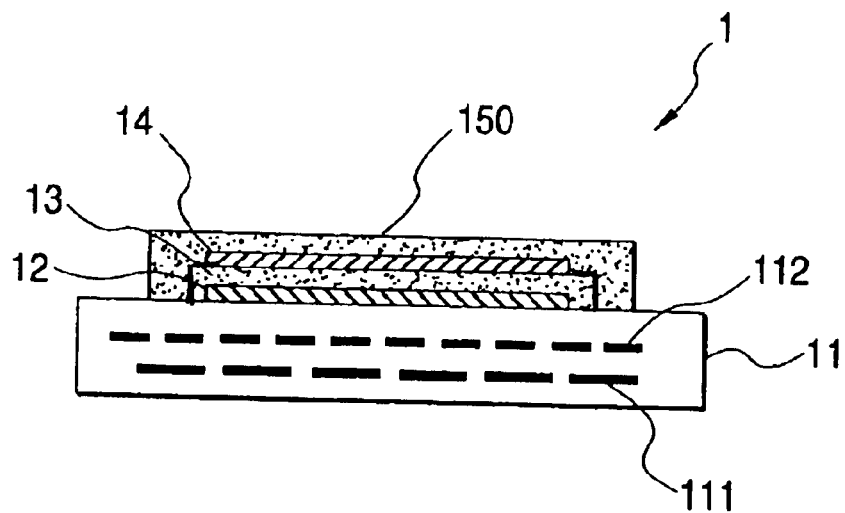

[FIGS. 9a and 9b]

(9a) Schematic perspective view showing a humidity sensor having a protective layer. (9b) Cross-sectional view of the humidity sensor taken along line A-A' in FIG. 9a.

DESCRIPTION OF REFERENCE NUMERALS

1: humidity sensor
11: insulating substrate
111: heater
112: temperature measurement resistor
12: lower electrode
13: moisture-sensitive layer
14: upper electrode
15: comblike electrode
121, 141, 151, 152: output lead wires connected to electrodes
2: air cylinder
31: mass flow (wet)
32: mass flow (dry)
4: thermostatic chamber
51: first saturated bath
52: second saturated bath
6: evaluation container
7: temperature-humidity detection apparatus
150: protective layer

DETAILED DESCRIPTION OF THE INVENTION

A humidity sensor of the present invention contains an insulating substrate, a detection electrodes, and a moisture-sensitive layer, and is characterized in that the moisture-sensitive layer is formed of a porous material and has a thickness not greater than 200 μm.

No particular limitations are imposed on an insulating material used for forming the aforementioned "insulating substrate." The insulating substrate may be formed from a ceramic material, a resin, or a like material. Of these materials, a ceramic material, which exhibits most excellent heat resistance among these materials, is preferred. Examples of such a ceramic material include $Al_2O_3$ and $ZrO_2$. Of these ceramic materials, alumina, which exhibits excellent insulating property and mechanical strength and is advantageous in terms of cost, is more preferred. No particular limitations are imposed on the thickness and planar dimensions of the insulating substrate, but the substrate can be formed into a rectangular platy body having a thickness of 0.3 to 2.0 mm, a width of 3 to 8 mm, and a length of 10 to 50 mm.

The aforementioned "detection electrodes" is formed from an electrically conductive material, and preferably contains a predominant amount (preferably, 50 to 99%) of at least one noble metal selected from Au, Ag, Ru, Rh, Pd, Os, Ir, and Pt. Of these noble metals, Pt or Au is more preferred. Particularly, Pt is the most preferred, since Pt is not easily oxidized at high temperature, is not diffused in the moisture-sensitive layer, and has a sufficiently high melting point. Therefore, when the detection electrodes are formed from Pt, the humidity sensor exhibits further enhanced durability.

The detection electrodes may be formed from an alloy containing two or more of above-described noble metals. For example, a combination of Pt and Rh is useful, since evaporation of Pt at high temperature is suppressed. The electrodes formed from a noble metal may contain other components, so long as such "other components" do not greatly affect the properties of the electrodes. The term "predominant" or "predominantly" used in relation to noble metal content means, for example, that 100 parts by mass (weight) of detection electrodes contains a noble metal in an amount of not less than 75 parts by mass, preferably not less than 85 parts by mass.

Preferably, each of the detection electrodes predominantly contains a noble metal and is formed of a porous material. When the moisture-sensitive layer and the detection electrodes are both formed of a porous material, a gas to be measured can easily and uniformly diffuse in the moisture-sensitive layer and the detection electrodes, whereby response of the humidity sensor can be enhanced. Preferably, in the humidity sensor, diffusion of a gas to be measured is not limited within the detection electrodes, whereby response of the humidity sensor can be further enhanced. Methods for attaining the above include a method in which each of the detection electrodes is rendered thinner as compared with the moisture-sensitive layer and a method in which each of the detection electrodes is enhanced in gas permeability than the moisture-sensitive layer.

In order to enhance gas permeability of the detection electrodes, noble metal grains contained in the detection electrodes are rendered greater in average grain size than grains of a moisture sensitive material used for forming the moisture-sensitive layer. As a result, the detection electrodes can assume the form of a porous material which has an average pore size greater than that of the moisture-sensitive layer, whereby response of the moisture sensor can be enhanced as in the case where thin detection electrodes are employed. The average grain size of moisture sensitive material grains, the average grain size of noble metal grains, the average pore size of the moisture-sensitive layer, and the average pore size of the detection electrodes can be calculated from grain sizes and pore sizes obtained through electron micrography on a section of the moisture-sensitive layer and a section of the detection electrode. The diameter of pores in the upper electrode and the lower electrode each preferably fall within the range of from 0.5 μm to 20 μm. The diameter of pores in the moisture-sensitive layer preferably fall within the range of from 0.05 μm to 1 μm. In order to obtain an upper electrode and a lower electrode having desired moisture permeability and electrical conductivity, it is preferred that the upper electrode and the lower electrode each contains a particulate ceramic such as particulate alumina and particulate zirconia incorporated therein in an amount of from 1 to 20% by weight. The reason for the restriction of the content of particulate ceramic to not smaller than 1% by weight is to exert a sufficient effect of improving the moisture permeability of the various electrodes. The reason for the restriction of the content of particulate ceramic to not greater than 20% by weight is to assure the prevention of malconduction of the various electrodes.

Diffusion of a gas to be measured in the detection electrodes is also influenced by a material used for forming the electrodes. In some cases, a material used for forming the electrodes may contain a glass component and a sintering aid which contains an alkaline earth metal element. Such components are effective for facilitating firing at low temperature and for stabilizing the electrodes, but hinder diffusion of a gas to be measured. Therefore, preferably, the detection electrodes predominantly contains a noble metal not containing such components. When the detection electrodes is specified in terms of thickness, average pore size, and material as described above, diffusion of a gas to be measured within the detection electrodes can hardly be limited. A sintering aid to be used is preferably a compound of excellent thermal stability, such as alumina or zirconia, thereby enhancing adhesion between the detection electrodes and the insulating substrate or the moisture-sensitive layer.

Figure 1A:
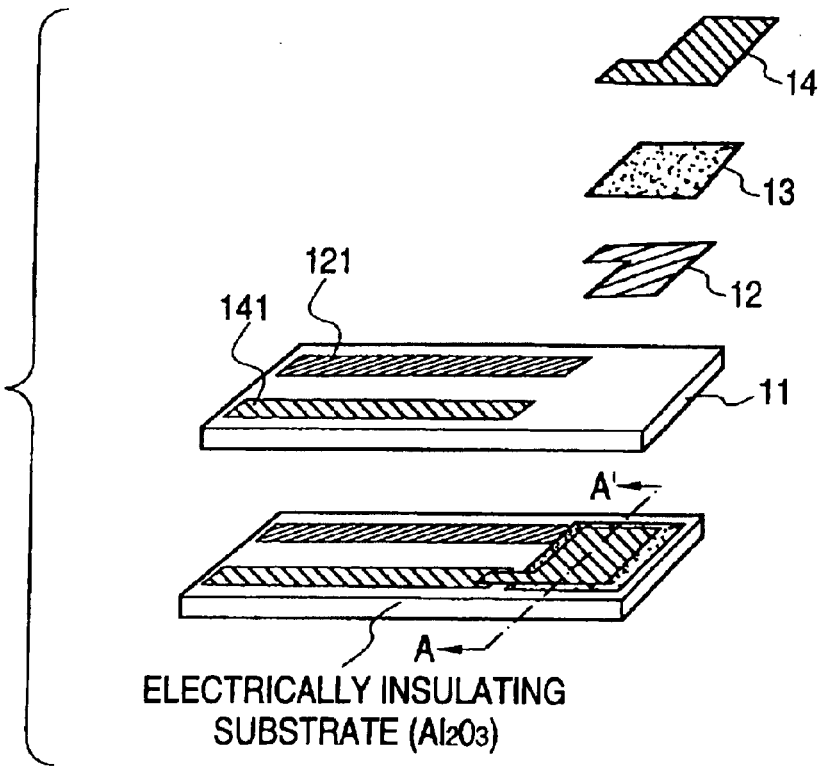
[FIGS. 1a and 1b]

The planar shape of the detection electrodes is not particularly limited, but may be circular, elliptical, or, as shown in FIG. 1a, rectangular. Alternatively, the detection electrodes may assume a comblike form as shown in FIGS. 2a to 2c. Since portions of the detection electrodes which are not in contact with the moisture-sensitive layer do not function as the detection electrodes, the moisture-sensitive layer is preferably in contact with the entire surfaces of the detection electrodes. A pair of comblike electrodes, or the lower electrode formed on the lower surface of the moisture-sensitive layer and the upper electrode formed on the upper surface of the moisture-sensitive layer are not necessarily formed from the same noble metal, but the electrodes are preferably formed from the same noble metal, since the process for forming the electrodes can be simplified, and simultaneous firing of the electrodes can be carried out easily.

The aforementioned "moisture-sensitive layer" may be formed from a variety of moisture sensitive materials. Examples of the moisture sensitive materials include moisture sensitive ceramic materials, such as $Al_2O_3$, $Al_2O_3$—$TiO_2$—$SnO_2$, $MgCr_2O_4$—$TiO_2$, $TiO_2$—$V_2O_5$, $ZrCr_2O_4$—$LiZrVO_4$, $ZnCrO_4$, $TiO_2$—$SnO_2$, and NASICON. When the moisture-sensitive layer is formed from a moisture sensitive material containing a plurality of oxides, the proportions of the oxides are not particularly limited; i.e., the moisture-sensitive layer may be formed from a generally used moisture sensitive material.

The moisture-sensitive layer is formed of a porous material and has a thickness not greater than 200 μm. When the thickness of the moisture-sensitive layer exceeds 200 μm, response time at the time of 62.3% response (time constant τ=1), which will be described later in Examples, exceeds 2 sec, resulting in impaired response. The thickness is preferably not greater than 100 μm, particularly preferably not greater than 75 μm, further preferably not greater than 50 μm. The thickness can also be as small as not greater than 30 μm. When the thickness of the moisture-sensitive layer is not greater than 50 μm, response time at the time of 62.3% response can be sufficiently short; specifically, not longer than 1.5 sec at a thickness not greater than 50 μm, and not longer than 1.3 sec at a thickness not greater than 30 μm. In view of prevention of short circuit when the electrodes are formed on the upper and lower surfaces of the moisture-sensitive layer, attainment of sufficient durability in the course of use, and easy fabrication, among other factors, the thickness of the moisture-sensitive layer is preferably not less than 5 μm, particularly preferably not less than 10 μm.

The thin moisture-sensitive layer yields another effect of reducing thermal stress, thereby enhancing thermal shock resistance. In the humidity sensor, the insulating substrate, the detection electrodes, and the moisture-sensitive layer differ in material and thermal expansion coefficient. Thus, when the detection electrodes and the moisture-sensitive layer are thick in relation to the insulating substrate, thermal stress induced by thermal expansion increases, potentially resulting in cracking, chipping, or a like defect, possibly leading to breakage.

According to the present invention, the moisture-sensitive layer is rendered thin, and each of the detection electrodes is rendered thinner as compared with the moisture-sensitive layer, whereby thermal stress can be sufficiently reduced to thereby provide a humidity sensor having excellent durability. No particular limitation is imposed on the ratio between the thickness ($t_m$) of the moisture-sensitive layer and the thickness ($t_e$) of each of the detection electrodes, $t_m/t_e$, but the ratio is preferably from 1.5 to 3, particularly preferably from 1.8 to 2.2. No particular limitation is imposed on the thicknesses of the electrodes, but an excessively thin electrode is unfavorable for attaining sufficient adhesion of the entire electrode surface to the moisture-sensitive layer. When the detection electrodes are composed of an upper electrode and a lower electrode, no particular limitation is imposed on the thickness ratio therebetween. The upper and lower electrodes may assume similar thicknesses.

Employment of a thin moisture-sensitive layer and thin detection electrodes can greatly reduce electrical resistance of the moisture-sensitive layer. The humidity sensor of the present invention can be used in, for example, an exhaust pipe of an automobile or a fuel feed pipe of a fuel cell. In such an application, an atmosphere surrounding the humidity sensor is generally full of electrical noise. Therefore, a conventional humidity sensor, whose moisture-sensitive layer is high in electrical resistance, requires installation of a capacitor or a like component in a control circuit, or employment of a filter circuit. However, employment of a thin moisture-sensitive layer and thin detection electrodes reduces the electrical resistance of the moisture-sensitive layer to about from 1/10 to 1/100 in comparison with the conventional level, thereby obviating employment of a capacitor, a filter circuit, or a like component.

The humidity sensor of the present invention, including the insulating substrate, the detection electrodes, and the moisture-sensitive layer, can be used in practice, if the sensor has lead wires connected to and extending from the detection electrodes, in order to obtain output from the sensor. However, preferably, a heater is provided in the insulating substrate. When the humidity sensor is periodically heated by means of the heater, moisture and other impurities that have invaded the moisture-sensitive layer can be removed completely. Through this removal, the moisture-sensitive layer is always maintained in a clean state, accuracy in detection by the sensor is enhanced, and the sensor maintains excellent output characteristics over a long period of time. Even in case that the humidity is very high, dew condensation onto the sensor can be prevented by operating the heater.

In the humidity sensor which measures the moisture content of an atmosphere at absolute zero temperature on the basis of change in the resistance of the moisture-sensitive layer, the resistance of the moisture-sensitive layer changes in accordance with the temperature of an atmosphere to be measured; i.e., the resistance of the layer has temperature dependency. Therefore, preferably, a temperature measurement resistor is provided within the insulating substrate. Change in the resistance of the moisture-sensitive layer with temperature is corrected by the temperature measurement resistor, and thus humidity can be detected at high accuracy, independent of the temperature of the atmosphere.

Preferably, the heater and the temperature measurement resistor are provided in the insulating substrate so as to be located at least partly below the moisture-sensitive layer. When the heater is provided at least partly below the moisture-sensitive layer, the entirety of the moisture-sensitive layer is easily heated in a substantially uniform manner, moisture and other impurities that have invaded the moisture-sensitive layer can be removed efficiently, and the power consumption required for heating the layer can be reduced to the greatest possible extent. Meanwhile, through provision of the temperature measurement resistor at least partly below the moisture-sensitive layer, the temperature of an atmosphere can be measured at a position which is substantially the same as the position at which the humidity is detected, without being affected by heat conduction of the insulating substrate. Therefore, accuracy in humidity detection can be further enhanced.

Even when the humidity sensor of the present invention is used in an atmosphere containing a small amount of oxygen and containing a considerable amount of reducing gas, the sensor maintains excellent performance over a long period of time. The phrase "the amount of oxygen is small" refers to a state, for example, concentration of about $10^{-9}$ to $10^{-20}$ atm. The term "an atmosphere containing reducing gas" refers to an atmosphere containing reducing gas in a certain amount or more such that the reducing gas can bring about chemical equilibrium.

In the humidity sensor of the present invention, the moisture-sensitive layer is thin, and each of the detection electrodes is thinner than the moisture-sensitive layer, thereby facilitating diffusion of a gas to be measured and providing highly good response. This will be described below in detail.

Figure 7:
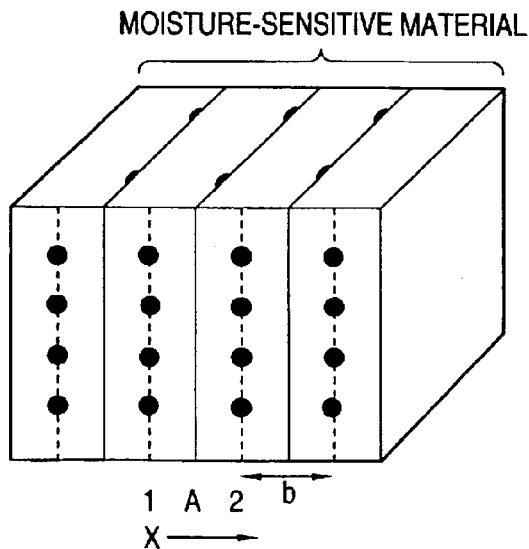

In application to measurement in a specific atmosphere that exhibits significant temperature variation and low oxygen concentration, as in an exhaust pipe of an automobile, or in a specific atmosphere that is highly reducing, as around an electrode or in a pipe of a fuel cell, a humidity sensor must exhibit highly good response. The most influential factor in relation to this response is diffusibility of a gas to be measured within the moisture-sensitive layer and within the detection electrodes. Diffusion of gas will next be described according to Fick's law, with reference to the schematic view of FIG. 7 showing diffusion of gas within the moisture-sensitive layer.

An elongated simple cubic lattice having a certain unit cross section will be discussed by way of example. When diffusion proceeds along the X axis, diffusion of gas from lattice plane 1 to lattice plane 2 is determined by the frequency of jumps of atoms to an adjacent lattice plane. When b represents a crystal face; $C_1$ and $C_2$ represent the number of diffusing atoms per unit volume in relation to lattice plane 1 and lattice plane 2, respectively; and $n_1$ and $n_2$ represent the number of atoms per unit area in relation to lattice plane 1 and lattice plane 2, respectively, $n_1$ is expressed by $n_1=C_1 b$, and $n_2$ is expressed by $n_2=C_2 b$. When the atoms jump to an adjacent lattice plane f times per unit time, the number of atoms jumping from lattice plane 1 to lattice plane 2 is expressed by $fn_1$. Since a simple cubic lattice involves six possible directions along which atoms jump, the number of atoms jumping from lattice plane 1 to lattice plane 2 is expressed by $fn_1/6$.

In the case of plane A located between lattice plane 1 and lattice plane 2, the number of atoms (flux) J passing through plane A along the X direction can be expressed by $$J=-fb/6*(C_2-C_1)$$

When the difference between $C_1$ and $C_2$ is small, $(C_2-C_1)$ can be expressed by use of a concentration gradient, as follows.

$$C_2-C_1=b*dC/dX$$

Then, the number of atoms J is expressed by $$J=-fb/6*b*dC/dX$$

Assuming that D is expressed by $D=fb^2/6$, the number of atoms J is expressed by $$J=-D*dC/dX$$

The above expression indicates that the amount of diffusion is proportional to a concentration gradient.

The above expressions indicate that the amount of diffusion can be adjusted by means of constant b, which depends on a moisture sensitive material to be used, mixing proportions among a plurality of moisture sensitive materials to be employed, the grain size of a moisture sensitive material to be used, or the like. However, when the amount of diffusion is adjusted through adjustment of such a material-related factor of the moisture-sensitive layer, the characteristics of the moisture-sensitive layer change greatly, resulting in difficulty in obtaining a humidity sensor having a predetermined moisture-sensing characteristic. Meanwhile, the amount of diffusion can be adjusted by means of adjusting the distance along the X direction; i.e., by means of adjusting the thickness of the moisture-sensitive layer. The thinner the moisture-sensitive layer, the greater the amount of diffusion. Increase in the amount of diffusion enhances response. Adjustment of the amount of diffusion through adjustment of the thickness of the moisture-sensitive layer, as employed by the humidity sensor of the present invention, can enhance response without involving change in moisture-sensing characteristic.

The humidity sensor of the invention preferably is made of a metal oxide or compound oxide and comprises a protective layer for covering the detection electrode and the moisture-sensitive layer. This protective layer makes it possible to inhibit the deterioration of the moisture-sensitive layer by harmful materials contained in the atmosphere to be measured. A metal oxide or compound oxide exhibits a high heat resistance and thus can form a humidity sensor which exhibits an excellent durability even when the atmosphere to be measured has a temperature as high as higher than 800° C. The kind of the metal oxide or compound oxide to be used is not limited. As the metal oxide or compound oxide there may be used alumina, spinnel, mullite, zirconia, titania, ceria, magnesia or the like. In particular, a ceramic which can difficultly undergo thermal shrinkage such as compound oxide (e.g., spinnel, mullite) is preferred.

The protective layer is made of a porous material having a porosity of preferably from 20% to 80%, particularly from 30% to 70%. When the porosity of the protective layer falls below 20%, the resulting protective layer is little permeable to moisture or the like, possibly deteriorating the responce of the humidity sensor to disadvantage. On the contrary, when the porosity of the protective layer exceeds 80%, harmful materials can easily permeate the protective layer, making it occasionally impossible to sufficiently inhibit the deterioration of the moisture-sensitive layer. The method for forming this protective layer is not specifically limited. The protective layer can be formed by an ordinary method for forming a metal oxide film or compound oxide film. In particular, the protective layer is preferably formed by a screen printing method, transfer method, spray coating method or dip coating method.

The protective layer, if the element is formed by opposing electrodes, is formed after the formation of the aforementioned electrodes so as to cover the element at least on the surface of the upper electrode and the area of the moisture-sensitive layer on which the upper electrode is not laminated. In this arrangement, the moisture-sensitive layer is sufficiently protected. The element is preferably covered by the protective layer on the whole surface thereof, including the edge face of the moisture-sensitive layer and the upper electrode. In other words, it is preferred that the peripheral edge of the protective layer be formed in contact with the surface of the insulating substrate. In this arrangement, the resulting humidity sensor can be provided with a better durability. The thickness of the protective layer is preferably from 10 $\mu$m to 200 $\mu$m, particularly from 20 $\mu$m to 100 $\mu$m. When the thickness of the protective layer is too small, harmful materials cannot be sufficiently caught. On the contrary, when the thickness of the protective layer exceeds 200 $\mu$m, the resulting protective layer is liable to peeling from the upper electrode or the like to disadvantage.

The sensor of the invention is characterized in that it is used to detect the state of a device for purifying the exhaust gas from an internal combustion engine (e.g., adsorbing material capable of adsorbing hydrocarbon and water content, exhaust gas purifying material such as three-way catalyst, HC trapping material comprising zeolite or the like, HC adsorption catalyst comprising a three-way catalyst and an HC trapping material) from the change of amount of water vapor in the exhaust gas. The invention discloses the usage of humidity sensor by way of example. For example, as disclosed in Japanese Patent Laid-Open No. 2001-323811, this type of an exhaust gas purifying device is used to purify the exhaust gas from an internal combustion engine. As disclosed in the above cited patent application disclosure, as the exhaust gas purifying device comprising an adsorbing material or the like deteriorates, the amount of water vapor downstream from the exhaust gas purifying device varies. Accordingly, by measuring the amount of water vapor in the exhaust gas downstream from the exhaust gas purifying device, the deterioration state of the exhaust gas purifying device can be detected.

EXAMPLES

The present invention will next be described in more detail by way of examples.
[1] Structure of Humidity Sensor Example 1

Figure 1B:
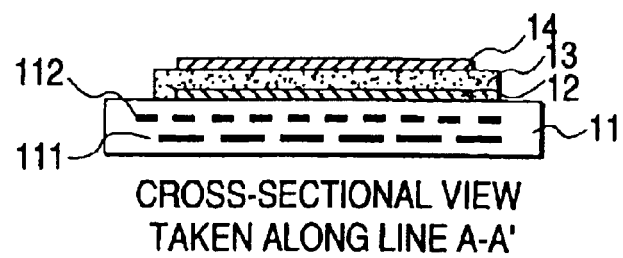

FIG. 1a is a perspective view showing an example of a humidity sensor 1 according to the present invention. FIG. 1b is a cross-sectional view taken along line A-A' in FIG. 1a.
(1) Insulating Substrate An insulating substrate 11 is formed from $Al_2O_3$, and has a thickness of 1.6 mm, a width of 4 mm, and a length of 45 mm. A heater 111 which is formed from Pt and assumes the shape of a bent strip is provided in the insulating substrate to be located at least partly below a moisture-sensitive layer at a position which is about ¼ the thickness of the substrate distant from the lower surface of the substrate. A temperature measurement resistor 112 which is formed from Pt and assumes the shape of a bent strip is provided in the insulating substrate to be located at least partly below the moisture-sensitive layer at a position which is about ¼ the thickness of the substrate distant from the upper surface of the substrate.
(2) Moisture-Sensitive Layer, Detection Electrodes, etc.

A lower electrode 12 formed from Pt is joined to the upper surface at one longitudinal end of the insulating substrate. The lower electrode 12 is formed by a porous material having an average grain diameter of from 2 $\mu$m to 3 $\mu$m and pores having a diameter of from 0.5 $\mu$m to 10 $\mu$m and comprising yttria-stabilized zirconia incorporated therein in an amount of 12% by weight. The lower electrode 12 has a thickness of 15 $\mu$m, a width of 2 mm, and a length of 2.5 mm. A portion of the lower electrode 12 is connected to an output lead wire 121. The lower surface of a moisture-sensitive layer 13 formed from a moisture sensitive ceramic material containing $Al_2O_3$ and predetermined amounts of $TiO_2$ and $SnO_2$ is joined to the entire surface of the lower electrode and a portion of the insulating substrate. The moisture-sensitive layer 13 is formed by a porous material having an average grain diameter of from 0.05 $\mu$m to 0.1 $\mu$m and comprising pores having a diameter of from 0.05 $\mu$m to 0.2 $\mu$mm. The moisture-sensitive layer 13 has a thickness of 30 $\mu$m, a width of 2.5 mm, and a length of 2.5 mm. An upper electrode 14 formed from Pt is joined to the upper surface of the moisture-sensitive layer which is opposite the lower electrode. The upper electrode 14 is formed by a porous material having an average grain diameter of from 2 $\mu$m to 3 $\mu$m and pores with a diameter of from 0.5 $\mu$m to 10 $\mu$m and comprising a yttria-stabilized zirconia incorporated therein in an amount of 12% by weight. The upper electrode 14 has a thickness of 15 $\mu$m, a width of 2 mm, and a length of 2.5 mm. A portion of the upper electrode extends to be connected to an output lead wire 141.

The heater is connected to a power supply source, and the temperature measurement resistor is connected to a temperature detection circuit. The power supply source, the temperature detection circuit, and lead wires connected thereto are not illustrated for the sake of simplicity.

Example 2

FIGS. 2a and 2b are a perspective view showing another example of the humidity sensor 1 according to the present invention. FIG. 2a is a perspective view showing comblike electrodes formed on the insulating substrate. FIG. 2c is a cross-sectional view of the humidity sensor taken along line A-A' in FIG. 2b.

In this humidity sensor, comblike electrodes 15 formed from Pt are joined to the upper surface at one longitudinal end of the insulating substrate 11. Each of the comblike electrodes 15 has a thickness of 15 $\mu$m, a width of 2 mm, a length of 2.5 mm, and a comb tooth width of 100 $\mu$m. End portions of the electrodes are connected to corresponding output lead wires 151 and 152. The lower surface of a moisture-sensitive layer 13 formed from a moisture sensitive ceramic material containing $Al_2O_3$ and predetermined amounts of $TiO_2$ and $SnO_2$ is joined to the entire surface of the comblike electrodes and a portion of the insulating substrate.
[2] Fabrication of Humidity Sensor
Fabrication of Humidity Sensor of Example 1
(1) Production of an Insulation Substrate having Output Lead Wires Thereon, and a Heater and a Temperature Measurement Resistor Disposed within the Substrate.

A slurry containing alumina powder was prepared, and alumina green sheets A, B, C, and D (the entirety to serve as an insulating substrate 11 after firing) (thickness of each sheet: 400 $\mu$m) were formed from the slurry through a doctor blade process. Thereafter, through screen printing, a Pt-containing paste for a heater was applied onto the upper surface of the alumina green sheet A, to thereby form a heater pattern (to serve as a heater 111 and wires to be connected to the power supply source (not illustrated) after firing).

Through screen printing, a Pt-containing paste for a temperature measurement resistor was applied onto a first surface of the alumina green sheet C, to thereby form a temperature measurement resistor pattern (to serve as a temperature measurement resistor 112 and wires to be connected to the temperature detection circuit (not illustrated) after firing). Furthermore, through screen printing, a Pt-containing paste for output lead wires was applied onto a first surface of the alumina green sheet D, to thereby form output lead wire patterns (to serve as output lead wires 121 and 141 after firing).

Subsequently, the alumina green sheets A to D were stacked on one another, such that 1) a second surface of the alumina green sheet D (the output lead wire patterns having been formed on the first surface thereof) came into contact with the first surface of the alumina green sheet C on which the temperature measurement resistor pattern had been formed; 2) a second surface of the alumina green sheet C came into contact with a first surface of the alumina green sheet B, the sheet B serving as an insulating layer for further reliably preventing contact between the heater pattern and the temperature measurement resistor pattern; and 3) a second surface of the alumina green sheet B came into contact with a first surface of the alumina green sheet A on which the heater pattern has been formed. The resultant product was pressed to thereby form a laminate. Thereafter, the resultant laminate was fired at 1,550° C. for two hours, to thereby produce an insulating substrate in which a heater and a temperature measurement resistor were provided.

The dimensions of the green sheets were determined such that 10 insulating substrates could be produced. Heater patterns, temperature measurement resistor patterns, and output lead wire patterns were formed in a number corresponding to the number of the substrates. The green sheets were stacked as described above, and the resultant laminate was cut into green substrates. The resultant green substrates were fired to thereby produce 10 insulating substrates simultaneously.

(2) Formation of Moisture-Sensitive Layer, Detection Electrodes, etc.

The moisture-sensitive layer, the detection electrodes, etc. were formed according to the following steps (i)–(iii).

(i) Formation of Lower Electrode

A platinum paste was applied, through printing, onto the surface of the insulating substrate 11 produced in (1) so as to form a lower electrode pattern having a thickness of 15 $\mu$m, a width of 2 mm, and a length of 2.5 mm. The resultant product was dried at 60° C. for one hour and was then fired at 1,200° C. for 10 minutes, to thereby form the lower electrode 12.

(ii) Formation of Moisture-Sensitive Layer

A paste for a moisture-sensitive layer, which had been prepared from a powder mixture containing $Al_2O_3$ powder and predetermined amounts of $TiO_2$ powder and $SnO_2$ powder, was applied, through printing, onto the surface of the lower electrode formed in (i). Thereafter, the resultant product was fired at 1,200° C. for two hours, to thereby form a moisture-sensitive layer 13 having a thickness of 30 $\mu$m, a width of 2.5 mm, and a length of 2.5 mm.

(iii) Formation of Upper Electrode

A platinum paste was applied, through printing, onto the surface of the moisture-sensitive layer formed in (ii) so as to form an upper electrode pattern having a thickness of 15 $\mu$m, a width of 2 mm, and a length of 2.5 mm. Simultaneously, a pattern for securing conduction between the upper electrode and the output lead wire 141 was printed onto one end face of the moisture-sensitive layer and onto the surface of the insulating substrate. The resultant product was dried at 60° C. for one hour and was then fired at 1,200° C. for 10 minutes, to thereby form the upper electrode 14, etc. Thus was fabricated the humidity sensor.

Fabrication of Humidity Sensor of Example 2

A humidity sensor of Example 2 was fabricated in a manner similar to that of Example 1 except for the following. A platinum paste was applied, through printing, onto the surface of the insulating substrate, which had been produced in a similar manner as in the case of fabrication of the humidity sensor of Example 1, so as to form comblike electrode patterns. The resultant product was dried and was then fired to thereby form the comblike electrodes. Thereafter, the paste for a moisture-sensitive layer which was used in fabrication of the humidity sensor of Example 1 was applied, through printing, onto the surface of the comblike electrodes. The resultant product was fired to thereby form the moisture-sensitive layer.

As described above, two kinds of humidity sensors of the present invention were fabricated. A humidity sensor of Comparative Example 1 was also fabricated in a manner similar to that of Example 1 except that a moisture-sensitive layer having a thickness of 400 $\mu$m was formed by a pelleting process.

Figure 8:
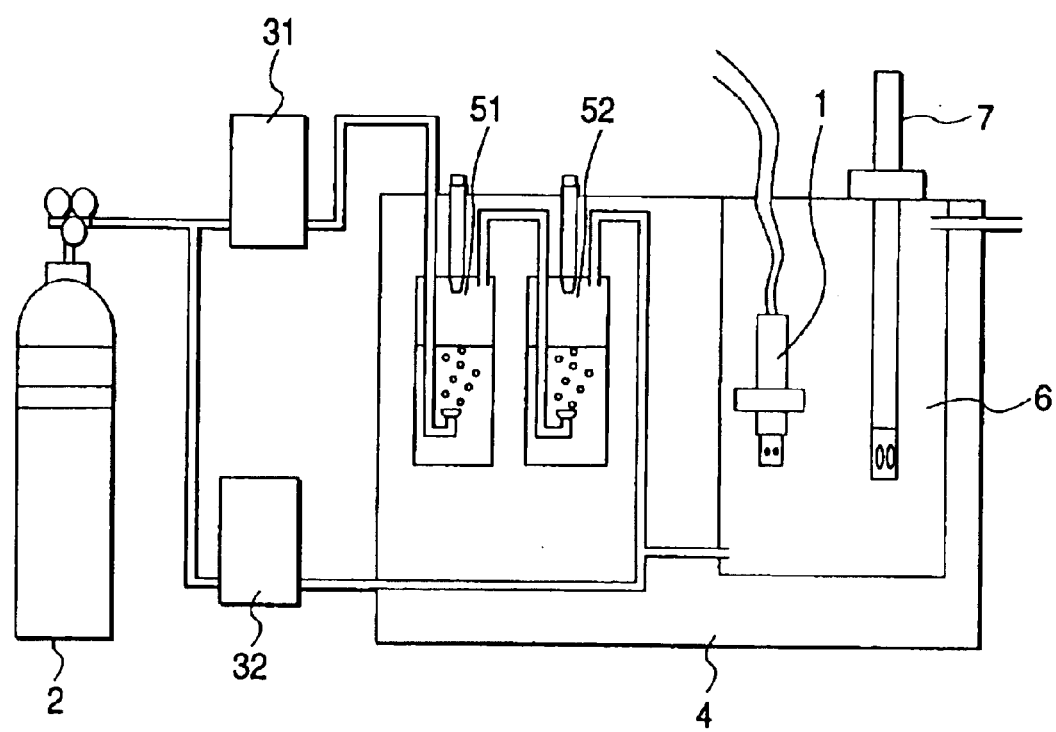

[3] Evaluation of Performance of Humidity Sensor (1) Evaluation of Initial Characteristics The humidity sensors of the present invention and the humidity sensor of Comparative Example, which were fabricated in [2], were evaluated for moisture-sensing characteristic and response characteristic by means of a diffluence method (in compliance with JIS Z 8806; see FIG. 8). This test evaluated how and to what extent a moisture-sensing characteristic and a response characteristic vary with the thickness of the moisture-sensitive layer. Evaluation conditions are described below.

(i) Moisture-Sensing Characteristic (Humidity Sensors of Example 1 and Comparative Example 1)

Figure 3:
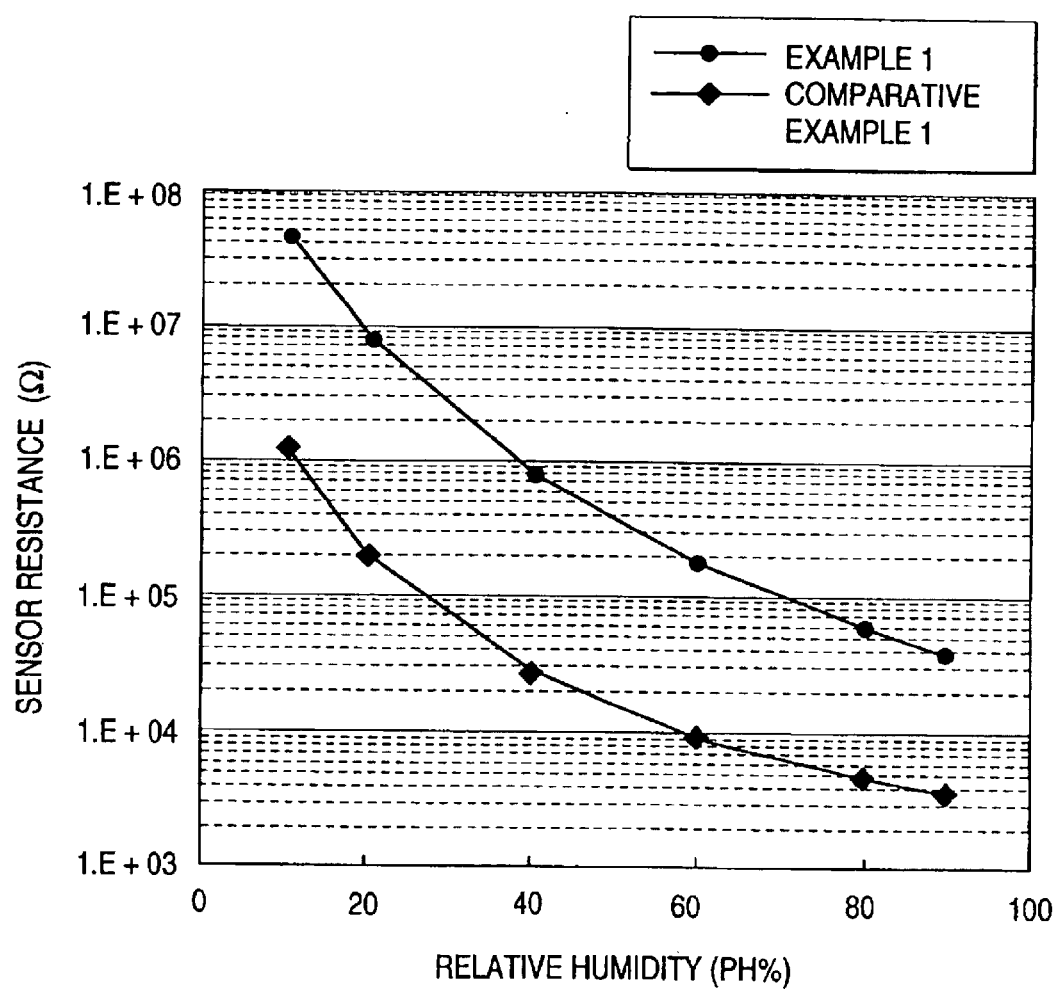

With air used as an evaluation gas, a sensor output was measured under the following conditions: temperature 20° C.; and relative humidity 10%, 20%, 40%, 60%, 80%, and 90%. In order to eliminate condensed water, the sensors were heated. After a measured resistance was stabilized, a sensor resistance was measured at the above humidity values, to thereby evaluate the sensors. The results are shown in FIG. 3.

(ii) Response Characteristic (Humidity Sensors of Example 1 and 2 and Comparative Example)

Figure 5:
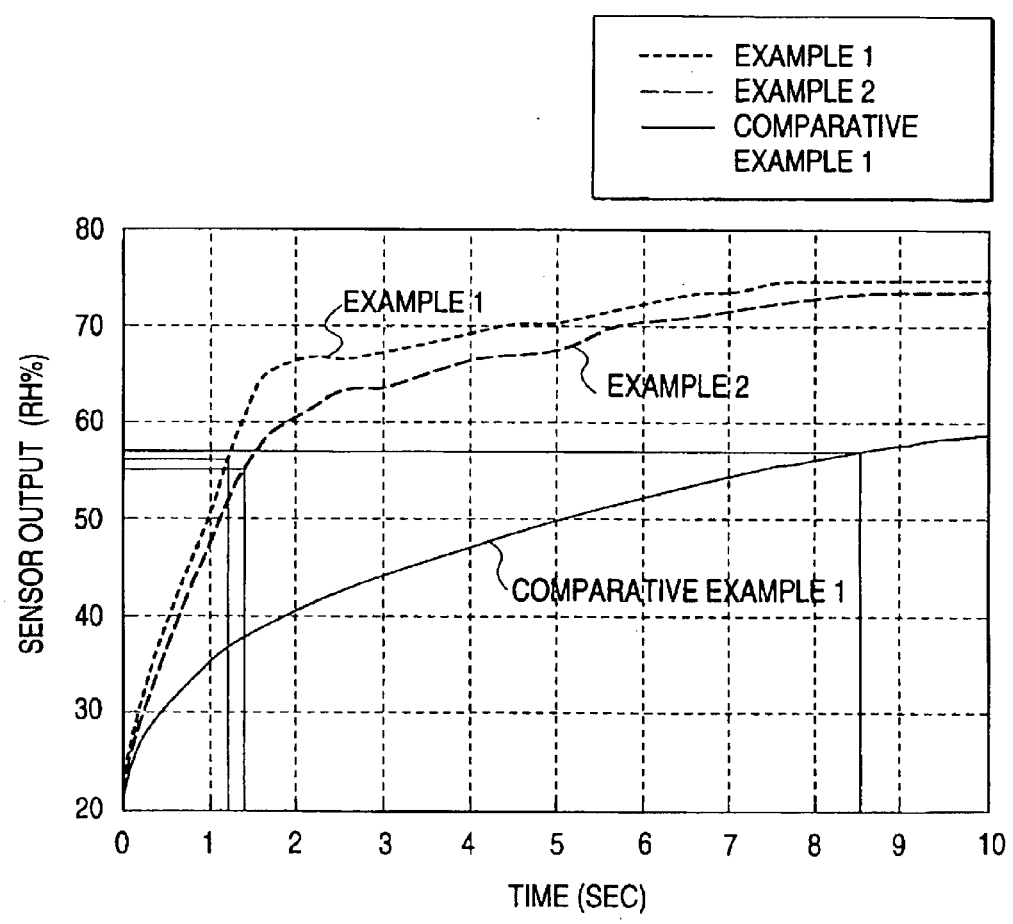

With air used as an evaluation gas, a sensor output was measured at a temperature of 20° C. while relative humidity was varied over the range of 20% to 80%. In order to eliminate condensed water, the sensors were heated. After a measured resistance was stabilized, a change in sensor resistance was measured while humidity was varied, to thereby evaluate the sensors. The results are shown in Table 1 and FIGS. 4 and 5. In FIGS. 4 and 5, the vertical axis indicates a sensor output that is reduced to humidity on the basis of resistance. Response characteristics of the sensors were compared on the basis of response time at the time of 63.2% response.

TABLE 1

| | Measured value | | Response characteristic [63.2% ($\tau = 1$)] | |
|---|---|---|---|---|
| | Humidity 20% | Humidity 80% | Ultimate humidity | Ultimate time |
| Example 1 | 21.84 | 75.78 | 55.82% | 1.4 sec |
| Example 2 | 23.55 | 75.73 | 56.42% | 1.2 sec |
| Comparative Example 1 | 24.55 | 76.98 | 57.58% | 8.6 sec |

As is apparent from FIG. 3, the humidity sensors of Example 1 and Comparative Example 1 exhibit substantially similar moisture-sensing characteristics. However, the sensor of Example 1 can reduce sensor resistance to about 1/30 that of Comparative Example 1. According to Table 1 and FIGS. 4 and 5, the humidity sensors of Examples 1 and 2 exhibit a response time which is a little in excess of 1 sec, thereby proving that the sensors exhibit excellent response. By contrast, the humidity sensor of Comparative Example 1 exhibits a response time of near 9 sec, indicating response thereof is greatly impaired because of the moisture-sensitive layer being thick.

(2) Interrelation between Thickness of Moisture-Sensitive Layer and Response (Example 1)

The interrelation between the thickness of the moisture-sensitive layer and response was evaluated by use of the humidity sensor of Example 1 in a manner similar to that in (1) (ii). The results are shown in FIG. 6.

Figure 6:
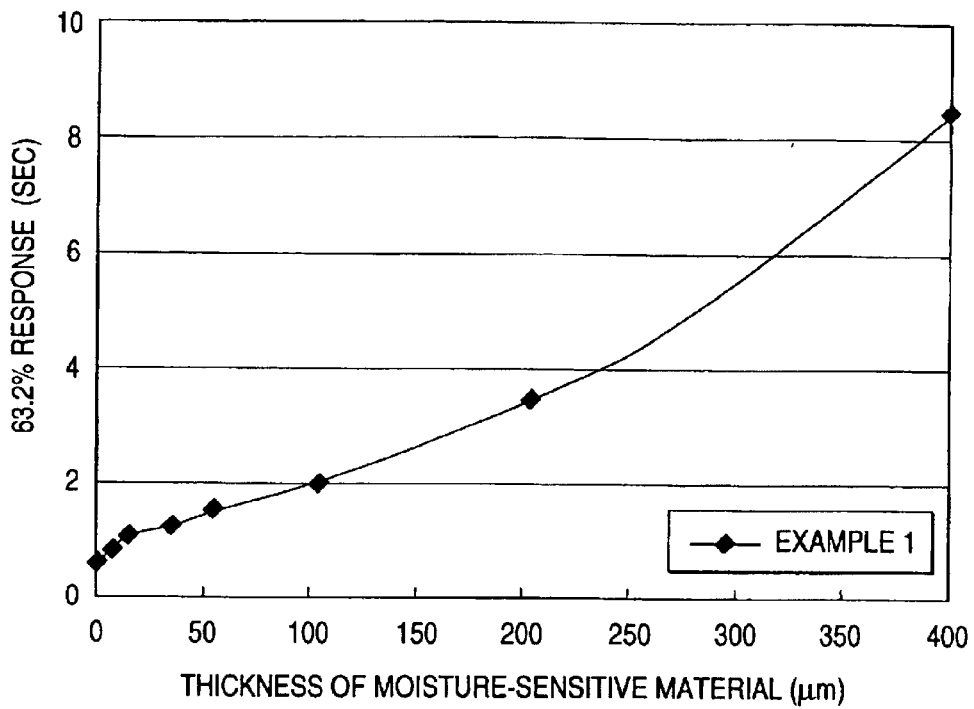

As is apparent from FIG. 6, as the thickness of the moisture-sensitive layer reduces, response is enhanced; and at a thickness of the moisture-sensitive layer of not greater than 100 $\mu$m, response time is not longer than 2 sec, indicating that the sensor exhibits excellent response. In this manner, as the moisture-sensitive layer becomes thinner, response is enhanced. However, as mentioned previously, when the moisture-sensitive layer is excessively thin, a short circuit between the upper and lower electrodes or a like problem arises. Therefore, preferably, the thickness of the moisture-sensitive layer is determined in consideration of such factors.

As shown in FIGS. 9a and 9b, a protective layer 150 made of spinel may be formed on the upper and side surfaces of the upper electrode and the moisture-sensitive layer. The peripheral edge of the protective layer is connected to the upper surface of the insulating substrate. In other words, the upper electrode, the moisture-sensitive layer and the lower electrode are entirely covered by the protective layer. The thickness of the protective layer is 30 $\mu$m. The porosity of the protective layer is 55%.

The formation of the protective layer 150 is accomplished by the following method. In some detail, a spinel powder is stirred in a dry process for 1 hour. To the powder were then added an acetone solution of ethyl cellosolve and n-butyl acetate in a proportion of 1/10 and 4.3/10, respectively, by mass. The mixture was then stirred in a wet process for 1 hour to prepare a paste for protective layer. Thereafter, the paste for protective layer was printed on the upper surface of the upper electrode formed at the aforementioned step (3) to form a pattern for protective layer to a thickness of 30 $\mu$m. Subsequently, the coated material was dried at a temperature of 60° C. for 1 hour, and kept and calcined at a temperature of 1,200° C. for 2 hours to form a protective layer 15.

By thus forming a protective layer having an excellent heat resistance made of a metal oxide or compound oxide, a humidity sensor can be obtained which exhibits an excellent durability because it undergoes no deterioration of properties due to harmful materials contained in the atmosphere to be measured even at high temperatures and gives a stabilized output even when used in an atmosphere having a low oxygen concentration and contains a reducing gas. Accordingly, the humidity sensor of the invention is useful particularly for the detection of the moisture content in a specific atmosphere as in the exhaust pipe of automobile, etc. or in fuel cell.

The present invention can provide a humidity sensor which produces stable output and exhibits excellent durability even in application to measurement in an atmosphere which exhibits low oxygen concentration, presence of a reducing gas, high temperature, and significant variations in, for example, gas flow rate and gas flow velocity. The humidity sensor can be fabricated by use of conventional materials and a conventional method, without need of special materials, apparatus, operation, etc. The humidity sensor is particularly useful for detecting the moisture content of a specific atmosphere, as in an exhaust pipe of a vehicle or as around an electrode of a fuel cell.

The entire disclosure of each and every foreign patent application from which the benefit of foreign priority has been claimed in the present application is incorporated herein by reference, as if fully set forth herein.

What is claimed is:

1. A humidity sensor comprising an insulating substrate, a moisture-sensitive layer, and at least two detection electrodes contacting the moisture-sensitive layer, wherein the moisture-sensitive layer is a porous layer and has a thickness not greater than 200 $\mu$m, and each of the detection electrodes comprises a noble metal and is formed of a porous material which has an average pore size greater than that of the moisture-sensitive layer.

2. The humidity sensor according to claim 1, wherein the moisture-sensitive layer has a thickness not greater than 50 $\mu$m.

3. The humidity sensor according to claim 1, wherein the detection electrodes comprise a lower electrode and an upper electrode; the lower electrode overlies the insulating substrate; the moisture-sensitive layer overlies the lower electrode such that an entire surface of the lower electrode except the surface covered with the insulating substrate is covered with the moisture-sensitive layer; and the upper electrode overlies the moisture-sensitive layer at a same position with the lower electrode in a laminating direction.

4. The humidity sensor according to claim 1, wherein a planar shape of the detection electrodes is a comblike planar shape; the detection electrodes overlay the insulating substrate; and the moisture-sensitive layer overlies the detection electrodes such that an entire surface of the detection electrodes except the surface covered with the insulating substrate is covered with the moisture-sensitive layer.

5. The humidity sensor according to claim 1, wherein a heater is provided in the insulating substrate.

6. The humidity sensor according to claim 1, wherein a temperature measurement resistor is provided in the insulating substrate.

7. The humidity sensor according to claim 5, wherein the heater is positioned at least partly within a region formed by projecting the moisture-sensitive layer in a laminating direction.

8. The humidity sensor according to claim 6, wherein the temperature measurement resistor is positioned at least partly within a region formed by projecting the moisture-sensitive layer in a laminating direction.

9. The humidity sensor according to claim 1, further comprising a protective coat that covers the detection electrodes and the moisture-sensitive layer, wherein the protective coat comprises one of a metal oxide and a compound oxide.

10. The humidity sensor according to claim 9, wherein the protective coat has a porosity of from 20% to 80%.

11. The humidity sensor according to claim 9, wherein the protective coat has a thickness of from 10 $\mu$m to 200 $\mu$m.

12. The humidity sensor according to claim 1, wherein the moisture-sensitive layer comprises $Al_2O_3$, $TiO_2$ and $SnO_2$.

13. The humidity sensor according to claim 12, wherein the moisture-sensitive layer has a thickness not greater than 50 $\mu$m.

14. The humidity sensor according to claim 12, wherein each of the detection electrodes comprises a noble metal and is formed of a porous material which has an average pore size greater than that of the moisture-sensitive layer.

15. The humidity sensor according to claim 12, wherein the detection electrodes comprise a lower electrode and an upper electrode; the lower electrode overlies the insulating substrate; the moisture-sensitive layer overlies the lower electrode such that an entire surface of the lower electrode except the surface covered with the insulating substrate is covered with the moisture-sensitive layer; and the upper electrode overlies the moisture-sensitive layer at a same position with the lower electrode in a laminating direction.

16. The humidity sensor according to claim 12, wherein a planar shape of the detection electrodes is a comblike planar shape; the detection electrodes overlay the insulating substrate; and the moisture-sensitive layer overlies the detection electrodes such that an entire surface of the detection electrodes except the surface covered with the insulating substrate is covered with the moisture-sensitive layer.

17. The humidity sensor according to claim 12, wherein a heater is provided in the insulating substrate.

18. The humidity sensor according to claim 12, wherein a temperature measurement resistor is provided in the insulating substrate.

19. The humidity sensor according to claim 17, wherein the heater is positioned at least partly within a region formed by projecting the moisture-sensitive layer in a laminating direction.

20. The humidity sensor according to claim 18, wherein the temperature measurement resistor is positioned at least partly within a region formed by projecting the moisture-sensitive layer in a laminating direction.

21. The humidity sensor according to claim 12, further comprising a protective coat that covers the detection electrodes and the moisture-sensitive layer, wherein the protective coat comprises one of a metal oxide and a compound oxide.

22. The humidity sensor according to claim 21, wherein the protective coat has a porosity of from 20% to 80%.

23. The humidity sensor according to claim 21, wherein the protective coat has a thickness of from $10 \mu m$ to $200 \mu m$.

24. The humidity sensor according to claim 1, wherein the moisture-sensitive layer has a thickness of from 5 to $50 \mu m$.

25. The humidity sensor according to claim 12, wherein the moisture-sensitive layer has a thickness of from 5 to 50 $\mu m$.

* * * * *